US012616451B2

(12) United States Patent
Winkler-Ebner et al.

(10) Patent No.: US 12,616,451 B2
(45) Date of Patent: May 5, 2026

(54) METHOD AND SYSTEM FOR ARTIFACT REDUCTION BY MOVEMENT DETECTION

(71) Applicant: GE Precision Healthcare LLC, Waukesha, WI (US)

(72) Inventors: Heinz Winkler-Ebner, Tiefgraben (AT); Daniel Bauernfeind, Aurach (AT)

(73) Assignee: GE Precision Healthcare LLC, Waukesha, WI (US)

( * ) Notice: Subject to any disclaimer, the term of this patent is extended or adjusted under 35 U.S.C. 154(b) by 0 days.

(21) Appl. No.: 18/398,696

(22) Filed: Dec. 28, 2023

(65) Prior Publication Data

US 2025/0213227 A1     Jul. 3, 2025

(51) Int. Cl.
*A61B 8/00*          (2006.01)
*G06T 5/50*          (2006.01)

(52) U.S. Cl.
CPC .............. *A61B 8/5276* (2013.01); *G06T 5/50* (2013.01); *G06T 2207/10132* (2013.01)

(58) Field of Classification Search
CPC .................... A61B 8/5276; G06T 5/50; G06T 2207/10132
See application file for complete search history.

(56) References Cited

U.S. PATENT DOCUMENTS

| | | | |
|---|---|---|---|
| 8,582,848 B2 | 11/2013 | Funka-Lea et al. | |
| 9,392,993 B2 | 7/2016 | Wang et al. | |
| 10,456,116 B2 | 10/2019 | Duncan et al. | |
| 10,540,769 B2 | 1/2020 | Pintoffl et al. | |
| 10,564,281 B2 | 2/2020 | Abe et al. | |
| 10,679,349 B2 | 6/2020 | Nicolardi et al. | |
| 10,713,758 B2 | 7/2020 | kucewicz et al. | |
| 2012/0143058 A1 | 6/2012 | Powers et al. | |
| 2017/0358085 A1 | 12/2017 | Nicolardi et al. | |
| 2020/0175652 A1* | 6/2020 | Agarwal | G06T 5/20 |
| 2022/0167947 A1* | 6/2022 | Seth | G06N 20/00 |

FOREIGN PATENT DOCUMENTS

EP          4062838          9/2022

* cited by examiner

*Primary Examiner* — Amelie R Davis
(74) *Attorney, Agent, or Firm* — McAndrews, Held & Malloy, Ltd.; Daniel Bissing; David Bates

(57) ABSTRACT

Systems and methods for artifact reduction in ultrasound imaging comprising acquiring a sequence of ultrasound images using an ultrasound probe along an acquisition plane, tracking a movement of the ultrasound probe along the acquisition plane and a movement of one or more artifacts in the sequence of ultrasound images, identifying one or more artifacts in the sequence of ultrasound images using the movement of the ultrasound probe along the acquisition plane and the movement of the one or more artifacts, wherein the movement of the one or more artifacts is different from the movement of the ultrasound probe along the acquisition plane, and correcting the sequence of ultrasound images, by at least one of adjusting a gain of the artifacts or stitching artifact areas of the sequence of ultrasound images with non-artifact areas of the sequence of ultrasound images.

19 Claims, 7 Drawing Sheets

800

Acquire a sequence of ultrasound images along an acquisition plane          802

Track movement of the ultrasound probe along the acquisition plane          804

Track movement of the one or more artifacts in the sequence of ultrasound images          806

Identify one or more artifacts in the sequence of ultrasound images          808

Correct artifacts in the sequence of ultrasound images          810

METHOD AND SYSTEM FOR ARTIFACT REDUCTION BY MOVEMENT DETECTION

FIELD

Certain embodiments relate to ultrasound imaging. More specifically, certain embodiments relate to a method and system for obtaining ultrasound scans with artifact reduction by movement detection.

BACKGROUND

Ultrasound imaging is a medical imaging technique for imaging organs and soft tissues in a human body. Ultrasound imaging uses real time, non-invasive high frequency sound waves to produce two-dimensional (2D), three-dimensional (3D), and/or four-dimensional (4D) (i.e., real-time/continuous 3D images) images.

Ultrasound imaging is a powerful tool for visualization. Ultrasound images are acquired by an ultrasound probe that may be used to scan anatomical structures to produce ultrasound images. However, current methods and ultrasound systems for acquiring ultrasound images include artifacts such as reverbs and shadows.

Further limitations and disadvantages of conventional and traditional approaches will become apparent to one of skill in the art, through comparison of such systems with some aspects of the present disclosure as set forth in the remainder of the present application with reference to the drawings.

BRIEF SUMMARY

A system and/or method is provided for obtaining ultrasound scans with artifact reduction by movement detection, substantially as shown in and/or described in connection with at least one of the figures, as set forth more completely in the claims.

These and other advantages, aspects and novel features of the present disclosure, as well as details of an illustrated embodiment thereof, will be more fully understood from the following description and drawings.

DETAILED DESCRIPTION

Figure 1:
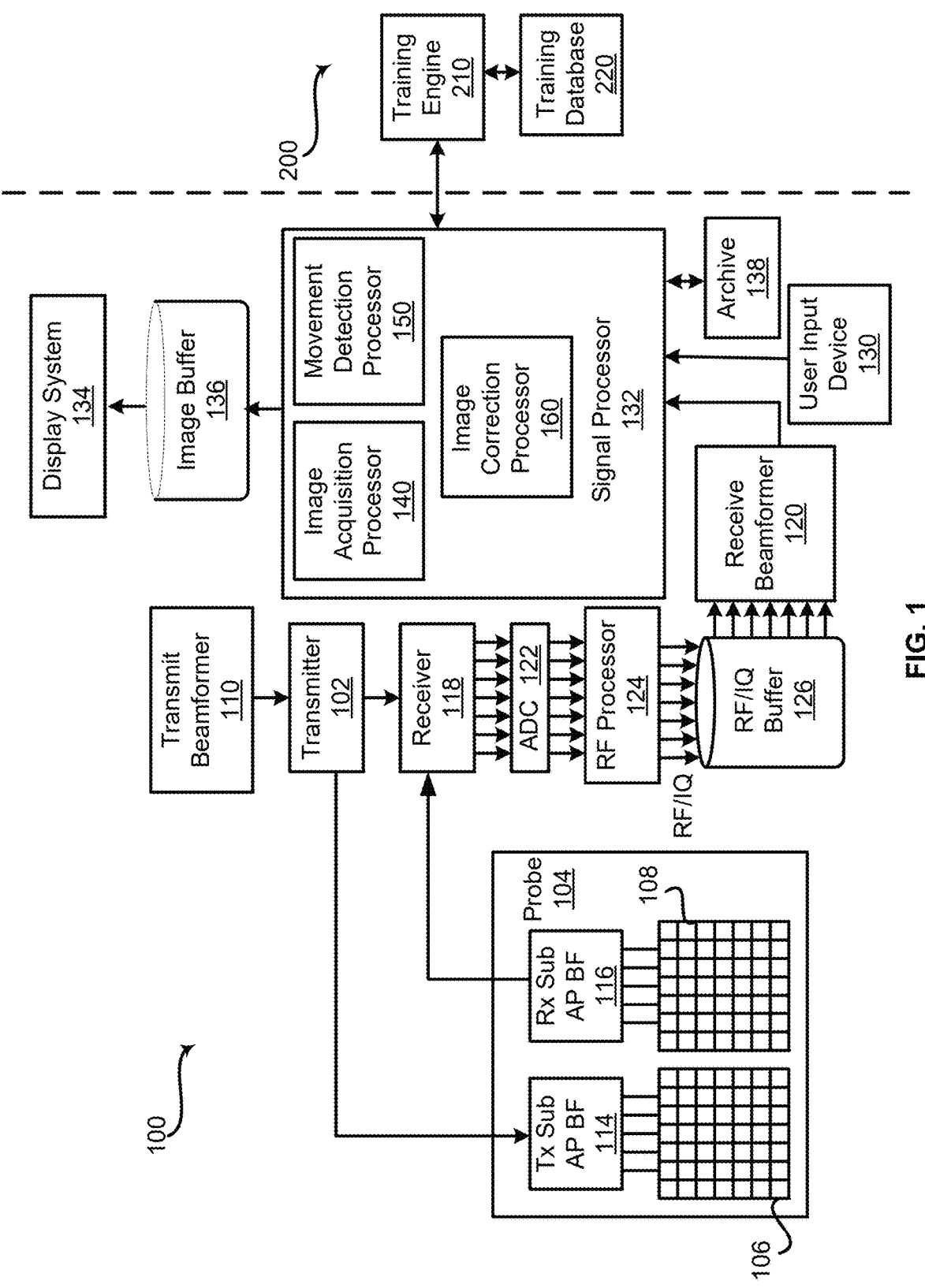
FIG. 1 is a block diagram of an exemplary ultrasound system that is operable to obtain ultrasound images with shadow and reverb reduction by movement detection, in accordance with various embodiments.

Certain embodiments may be found in a method and system for obtaining ultrasound scans with artifact reduction by movement detection. Aspects of the present disclosure have the technical effect of providing ultrasound images with improved quality by reducing artifacts such as shadows and reverbs. Various embodiments have the technical effect of detecting artifacts such as shadows and reverbs by measuring the movement of the acquisition and the movement of the artifacts in a sequence of ultrasound images obtained along an acquisition plane.

Certain embodiments have the technical effect of correcting artifacts in ultrasound images by adjusting the gain of the artifacts, employing stitching methods, and/or border smoothing. Various embodiments have the technical effect of providing increased clarity and details in ultrasound images in real-time, thereby aiding in diagnosis using ultrasound images and decreasing ultrasound scanning time for patients in many situations.

The foregoing summary, as well as the following detailed description of certain embodiments will be better understood when read in conjunction with the appended drawings. To the extent that the figures illustrate diagrams of the functional blocks of various embodiments, the functional blocks are not necessarily indicative of the division between hardware circuitry. Thus, for example, one or more of the functional blocks (e.g., processors or memories) may be implemented in a single piece of hardware (e.g., a general-purpose signal processor or a block of random access memory, hard disk, or the like) or multiple pieces of hardware. Similarly, the programs may be stand-alone programs, may be incorporated as subroutines in an operating system, may be functions in an installed software package, and the like. It should be understood that the various embodiments are not limited to the arrangements and instrumentality shown in the drawings. It should also be understood that the embodiments may be combined, or that other embodiments may be utilized, and that structural, logical, and electrical changes may be made without departing from the scope of the various embodiments. The following detailed description is, therefore, not to be taken in a limiting sense, and the scope of the present disclosure is defined by the appended claims and their equivalents.

As used herein, an element or step recited in the singular and preceded with the word "a" or "an" should be understood as not excluding plural of said elements or steps, unless such exclusion is explicitly stated. Furthermore, references to "an exemplary embodiment," "various embodiments," "certain embodiments," "a representative embodiment," and the like are not intended to be interpreted as excluding the existence of additional embodiments that also incorporate the recited features. Moreover, unless explicitly stated to the contrary, embodiments "comprising", "including", or "having" an element or a plurality of elements having a particular property may include additional elements not having that property.

Also as used herein, the term "image" broadly refers to both viewable images and data representing a viewable image. However, many embodiments generate (or are configured to generate) at least one viewable image. In addition, as used herein, the phrase "image" is used to refer to an ultrasound mode, which can be one-dimensional (1D), two-dimensional (2D), three-dimensional (3D), or four-dimensional (4D), and comprising Brightness mode (B-mode), Motion mode (M-mode), Color Motion mode (CM-mode), Color Flow mode (CF-mode), Pulsed Wave (PW) Doppler, Continuous Wave (CW) Doppler, Contrast Enhanced Ultrasound (CEUS), and/or sub-modes of B-mode and/or CF-mode such as Harmonic Imaging, Shear Wave Elasticity Imaging (SWEI), Strain Elastography, Tissue Velocity Imaging (TVI), Power Doppler Imaging (PDI), B-flow, Micro Vascular Imaging (MVI), Ultrasound-Guided Attenuation Parameter (UGAP), and the like. The term, "ultrasound image," as used herein, is used to refer to ultrasound image and/or ultrasound image volumes, such as a bi-plane image, a single 2D image, a rendering of a volume (3D/4D), 2D bi-plane image slices extracted from a volume (3D/4D), and/or any suitable ultrasound image. In some examples, the ultrasound image may be a still image or an ultrasound clip. For purposes of this disclosure, the term "still image" may be used to refer to a single ultrasound frame, while the term "ultrasound clip" may be used to refer to a plurality of ultrasound frames acquired in sequence, each at a different point in time. When displayed, each of the ultrasound frames in an ultrasound clip is displayed in sequence, which allows the ultrasound clip to display motion in a manner similar to a movie. The ultrasound clip, which is also commonly referred to as a cine loop by those skilled in the art, may include either 2D or 3D ultrasound frames acquired over a period of time. In some examples, the ultrasound images and/or ultrasound clips may be displayed in real-time and/or may be stored in a computer readable medium for later retrieval.

Furthermore, the term processor or processing unit, as used herein, refers to any type of processing unit that can carry out the required calculations needed for the various embodiments, such as single or multi-core: CPU, Accelerated Processing Unit (APU), Graphic Processing Unit (GPU), Digital Signal Processor (DSP), Field-Programmable Gate Array (FPGA), Application-Specific Integrated Circuit (ASIC), or a combination thereof.

It should be noted that various embodiments described herein that generate or form images may include processing for forming images that in some embodiments includes beamforming and in other embodiments does not include beamforming. For example, an image can be formed without beamforming, such as by multiplying the matrix of demodulated data by a matrix of coefficients so that the product is the image, and wherein the process does not form any "beams". In addition, forming of images may be performed using channel combinations that may originate from more than one transmit event (e.g., synthetic aperture techniques).

In various embodiments, ultrasound processing to form images is performed, for example, including ultrasound beamforming, such as receive beamforming, in software, firmware, hardware, or a combination thereof. One implementation of an ultrasound system having a software beamformer architecture formed in accordance with various embodiments is illustrated in FIG. 1.

FIG. 1 is a block diagram of an exemplary ultrasound system 100 that is operable to obtain an ultrasound volume from bi-plane ultrasound scanning. Referring to FIG. 1, there is shown an ultrasound system 100 and a training system 200. The ultrasound system 100 comprises a transmitter 102, an ultrasound probe 104, a transmit beamformer 110, a receiver 118, a receive beamformer 120, analog-to-digital (A/D) converters 122, a radio frequency (RF) processor 124, a RF quadrature (RF/IQ) buffer 126, a user input device 130, a signal processor 132, an image buffer 136, a display system 134, and an archive 138.

The transmitter 102 may comprise suitable logic, circuitry, interfaces, and/or code that may be operable to drive an ultrasound probe 104. The ultrasound probe 104 may comprise a two-dimensional (2D) array of piezoelectric elements. In various embodiments, the ultrasound probe 104 may be a matrix array transducer or any suitable transducer operable to acquire 2D and/or 3D ultrasound image datasets. The ultrasound probe 104 may comprise a group of transmit transducer elements 106 and a group of receive transducer elements 108, that normally constitute the same elements. In certain embodiment, the ultrasound probe 104 may be operable to acquire ultrasound image data covering at least a substantial portion of an anatomy, such as an abdomen, a heart, a fetus, a lung, a blood vessel, or any suitable anatomical structure(s). The ultrasound probe 104 may be a curvilinear, convex, or phased array probe, as non-limiting examples.

The transmit beamformer 110 may comprise suitable logic, circuitry, interfaces and/or code that may be operable to control the transmitter 102 which, through a transmit sub-aperture beamformer 114, drives the group of transmit transducer elements 106 to emit ultrasonic transmit signals into a region of interest (e.g., human, animal, underground cavity, physical structure and the like). The transmitted ultrasonic signals may be back-scattered from structures in the object of interest, like blood cells or tissue, to produce echoes. The echoes are received by the receive transducer elements 108.

The group of receive transducer elements 108 in the ultrasound probe 104 may be operable to convert the received echoes into analog signals, undergo sub-aperture beamforming by a receive sub-aperture beamformer 116 and are then communicated to a receiver 118. The receiver 118 may comprise suitable logic, circuitry, interfaces and/or code that may be operable to receive the signals from the receive sub-aperture beamformer 116. The analog signals may be communicated to one or more of the plurality of A/D converters 122.

The plurality of A/D converters 122 may comprise suitable logic, circuitry, interfaces, and/or code that may be operable to convert the analog signals from the receiver 118 to corresponding digital signals. The plurality of A/D converters 122 are disposed between the receiver 118 and the RF processor 124. Notwithstanding, the disclosure is not limited in this regard. Accordingly, in some embodiments, the plurality of A/D converters 122 may be integrated within the receiver 118.

The RF processor 124 may comprise suitable logic, circuitry, interfaces, and/or code that may be operable to demodulate the digital signals output by the plurality of A/D converters 122. In accordance with an embodiment, the RF processor 124 may comprise a complex demodulator (not shown) that is operable to demodulate the digital signals to form I/Q data pairs that are representative of the corresponding echo signals. The RF or I/Q signal data may then be communicated to an RF/IQ buffer 126. The RF/IQ buffer 126 may comprise suitable logic, circuitry, interfaces, and/or code that may be operable to provide temporary storage of the RF or I/Q signal data, which is generated by the RF processor 124.

The receive beamformer 120 may comprise suitable logic, circuitry, interfaces and/or code that may be operable to perform digital beamforming processing to, for example, sum the delayed channel signals received from RF processor 124 via the RF/IQ buffer 126 and output a beam summed signal. The resulting processed information may be the beam summed signal that is output from the receive beamformer 120 and communicated to the signal processor 132. In accordance with some embodiments, the receiver 118, the plurality of A/D converters 122, the RF processor 124, and the beamformer 120 may be integrated into a single beam-former, which may be digital. In various embodiments, the ultrasound system 100 comprises a plurality of receive beamformers 120.

The user input device 130 may be utilized to input patient data, scan parameters, settings, select protocols and/or templates, select displacement parameters to acquire displacements in one more directions and/or rotational displacements, manipulate the acquired 3D volume, and the like. In an exemplary embodiment, the user input device 130 may be operable to configure, manage, and/or control operation of one or more components and/or modules in the ultrasound system 100. In this regard, the user input device 130 may be operable to configure, manage, and/or control operation of the transmitter 102, the ultrasound probe 104, the transmit beamformer 110, the receiver 118, the receive beamformer 120, the RF processor 124, the RF/IQ buffer 126, the user input device 130, the signal processor 132, the image buffer 136, the display system 134, and/or the archive 138. The user input device 130 may include button(s), rotary encoder(s), a touchscreen, motion tracking, voice recognition, a mousing device, keyboard, camera, and/or any other device capable of receiving a user directive. In certain embodiments, one or more of the user input devices 130 may be integrated into other components, such as the display system 134 or the ultrasound probe 104, for example. As an example, user input device 130 may include a touchscreen display.

The signal processor 132 may comprise suitable logic, circuitry, interfaces and/or code that may be operable to process ultrasound scan data (i.e., summed IQ signal) for generating ultrasound images for presentation on a display system 134. The signal processor 132 is operable to perform one or more processing operations according to a plurality of selectable ultrasound modalities on the acquired ultrasound scan data. In an exemplary embodiment, the signal processor 132 may be operable to perform display processing and/or control processing, among other things. Acquired ultrasound scan data may be processed in real-time during a scanning session as the echo signals are received. Additionally or alternatively, the ultrasound scan data may be stored temporarily in the RF/IQ buffer 126 during a scanning session and processed in less than real-time in a live or off-line operation. In various embodiments, the processed image data can be presented at the display system 134 and/or may be stored at the archive 138. The archive 138 may be a local archive, a Picture Archiving and Communication System (PACS), a remote archive, or any suitable device for storing images and related information.

The signal processor 132 may be one or more central processing units, microprocessors, microcontrollers, and/or the like. The signal processor 132 may be an integrated component, or may be distributed across various locations, for example. In an exemplary embodiment, the signal processor 132 may comprise an image acquisition processor 140, a movement detection processor 150, and an image correction processor 160. The signal processor 132 may be capable of receiving input information from a user input device 130 and/or archive 138, generating an output displayable by a display system 134, and manipulating the output in response to input information from a user input device 130, among other things. The signal processor 132, image acquisition processor 140, movement detection processor 150, and image correction processor 160 may be capable of executing any of the method(s) and/or set(s) of instructions discussed herein in accordance with the various embodiments, for example.

The ultrasound system 100 may be operable to continuously acquire ultrasound scan data at a frame rate that is suitable for the imaging situation in question. Typical frame rates range from 20-120 but may be lower or higher. The acquired ultrasound scan data may be displayed on the display system 134 at a display-rate that can be the same as the frame rate, or slower or faster. An image buffer 136 is included for storing processed frames of acquired ultrasound scan data that are not scheduled to be displayed immediately. Preferably, the image buffer 136 is of sufficient capacity to store at least several minutes' worth of frames of ultrasound scan data. The frames of ultrasound scan data are stored in a manner to facilitate retrieval thereof according to its order or time of acquisition. The image buffer 136 may be embodied as any known data storage medium.

The signal processor 132 may include an image acquisition processor 140 that comprises suitable logic, circuitry, interfaces, and/or code that may be operable to acquire ultrasound images of anatomical structures such as cardiac structures, gastroenterological structures, urological structures, reproductive structures, cardiac structures, pulmonary structures, and/or any suitable anatomical structures. The ultrasound images may be ultrasound images and/or ultrasound image volumes, such as a bi-plane image, a single 2D image, a rendering of a volume (3D/4D), 2D bi-plane image slices extracted from a volume (3D/4D), and/or any suitable ultrasound images. In some examples, the ultrasound images are still images and/or ultrasound clips.

In an exemplary embodiment, the image acquisition processor 140 may acquire ultrasound images using an ultrasound probe 104 that is moved across an anatomical structure. The image acquisition processor 140 may capture the ultrasound images along an acquisition plane. The ultrasound images may be obtained sequentially as the ultrasound probe 104 is moved across the anatomical structure. As the ultrasound images are captured, artifacts may be captured in the ultrasound images, such as reverbs and shadows. In some examples, shadows may be caused by structures with high ultrasound reflectivity (e.g. bones) and may create dark areas in ultrasound images as less ultrasound signal may pass through the structure. In some examples, reverbs may be caused by structures below a currently visible penetration depth and/or by secondary reflections. In some examples, reverbs may suggest structures at positions in the ultrasound images in positions where structures are not positioned. The ultrasound images may be presented on a display 134 and/or may be stored in an archive or other computer readable medium for later retrieval. Additionally and/or alternatively, the ultrasound images may be provided to the movement detection processor 150.

Figure 2:
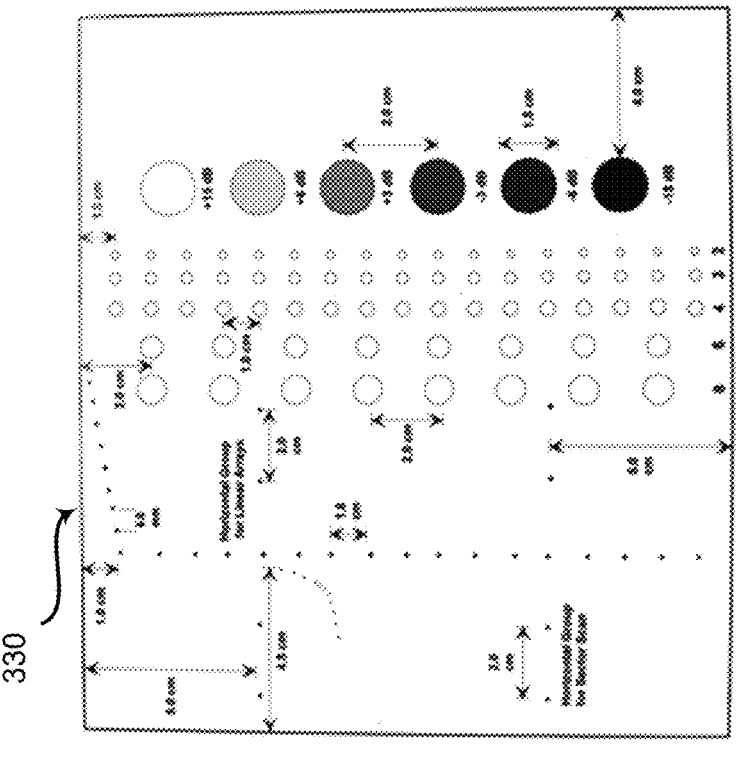
FIG. 2 provides an illustration of an ultrasound image and a schematic, in accordance with various embodiments.
Figure 2:
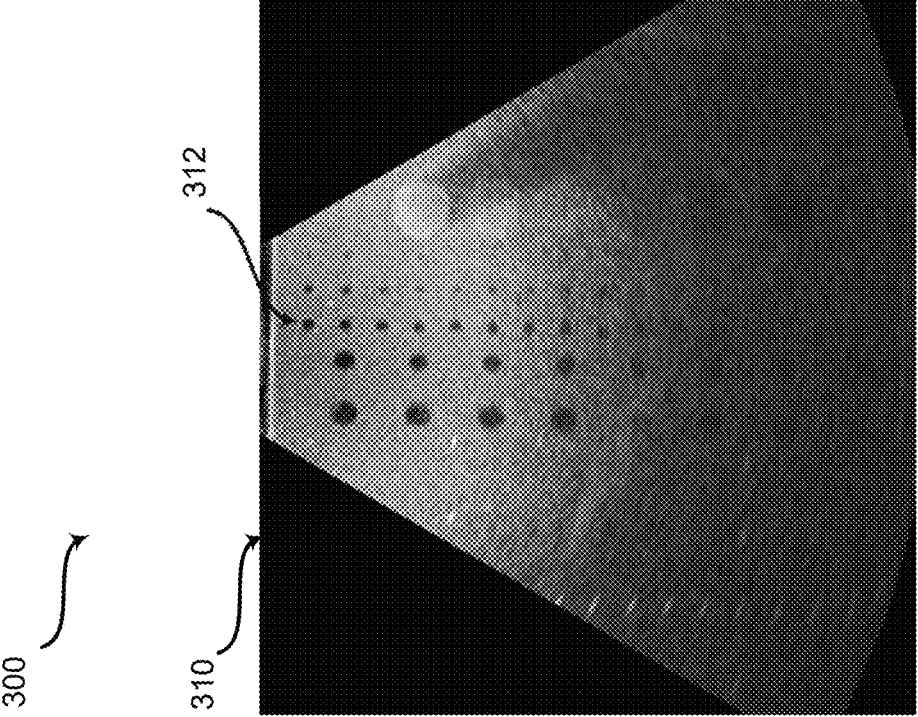

FIG. 2 provides an illustration 300 of an ultrasound image 310 and a schematic 330, in accordance with various embodiments. Ultrasound image 310 includes a phantom mimicking an anatomical structure 312 and a schematic 330 of the phantom. The ultrasound image 310 may be captured by the ultrasound probe 104 as the ultrasound probe 104 is moved across the anatomical structure 312 along an acquisition plane. The phantom schematic 330 provides details regarding the phantom representing an anatomical structure 312 used to acquire the ultrasound image 310. As the ultrasound probe 104 is moved across the anatomical structure 312, the image acquisition processor 140 captures a sequence of ultrasound images such as ultrasound image 310 while traveling along the acquisition plane.

Returning to FIG. 1, the signal processor 132 may include a movement detection processor 150 that comprises suitable logic, circuitry, interfaces, and/or code that may be operable to calculate movement information for the ultrasound probe 104, for the sequence of ultrasound images, and/or for artifacts in the sequence of ultrasound images obtained by the ultrasound probe 104. For example, the movement detection processor 150 may be configured to receive from the image acquisition processor 140, and/or retrieve from the archive 138 and/or any suitable data storage medium, a sequence of ultrasound images in order to calculate movement of the ultrasound probe 104 and/or the artifacts between each of the sequence of acquired ultrasound images.

In some examples, the movement detection processor 150 tracks the movement of the ultrasound probe 104 as the sequence of ultrasound images is captured by the ultrasound probe 104 and/or tracks the movement of the ultrasound probe 104 by measuring movement in the sequence of ultrasound images. For example, movement of the ultrasound probe 104 translates to movement in the sequence of ultrasound images. When measuring the movement of the ultrasound probe 104, rotations and translations may be detected in the acquisition plane. Movement of the ultrasound probe 104 may be calculated by an algorithm for optical flow, including panning and/or rotation of an image, using methods such as Lucas-Kanade or other similar methods. Additionally and/or alternatively, movement of the sequences of ultrasound images may be determined by directly detecting the motion of the ultrasound probe 104, for example, using a gyroscope or an accelerometer inside the ultrasound probe 104. The motion of the ultrasound probe 104 may be provided to the movement detection processor 150. In some examples, one or more thresholds are used to determine whether movement detected in the sequence of ultrasound images is out of the acquisition plane and/or whether objects captured in the sequence of ultrasound images are in motion. Movements of the ultrasound probe 104 captured by the movement detection processor 150 may be stored and/or provided to the image correction processor 160.

Figure 3:
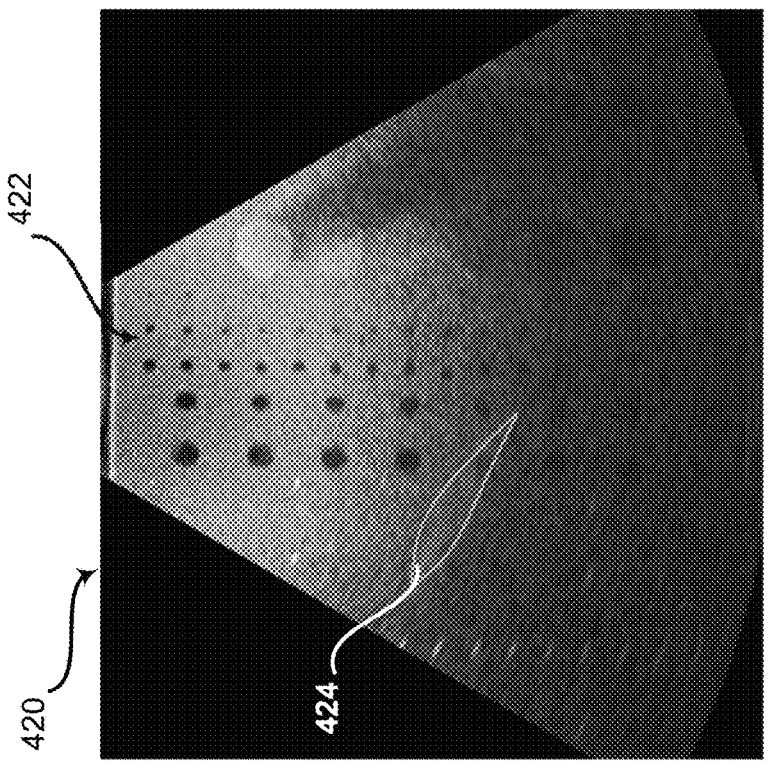
FIG. 3 is an example illustration 400 of ultrasound images 410 430 including artifacts, in accordance with various embodiments.
Figure 3:
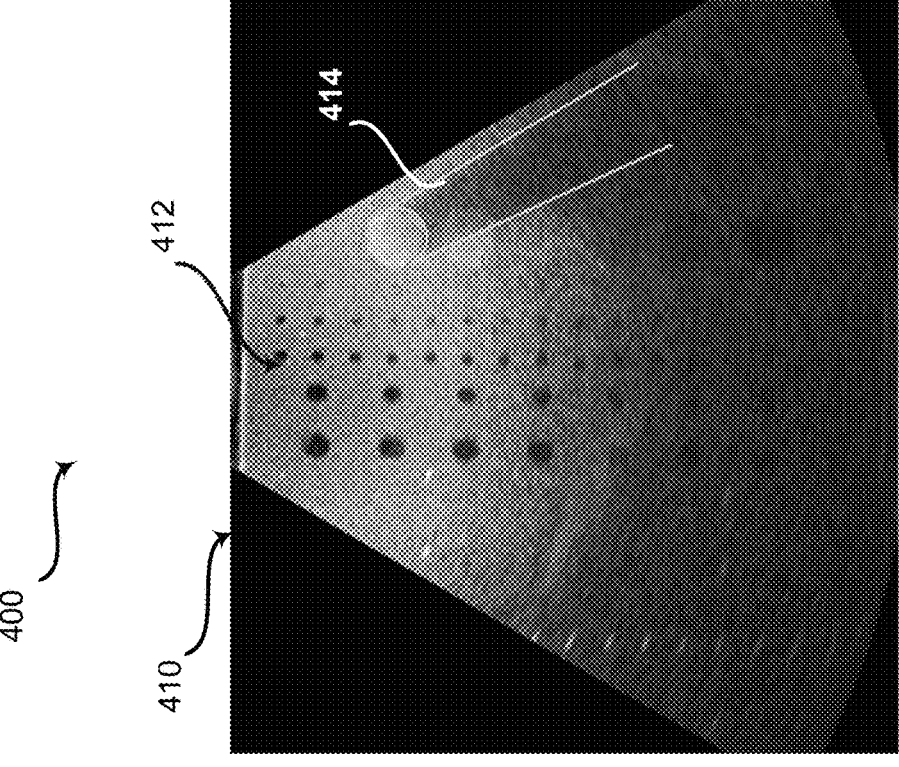

FIG. 3 is an example illustration 400 of ultrasound images 410 430 including artifacts, in accordance with various embodiments. The illustration 400 includes an ultrasound image 410 including a phantom representing an anatomical structure 412 and includes an artifact such as a shadow 414. Ultrasound image 420 includes a phantom representing anatomical structure 422 and includes an artifact such as reverb 424.

Figure 4:
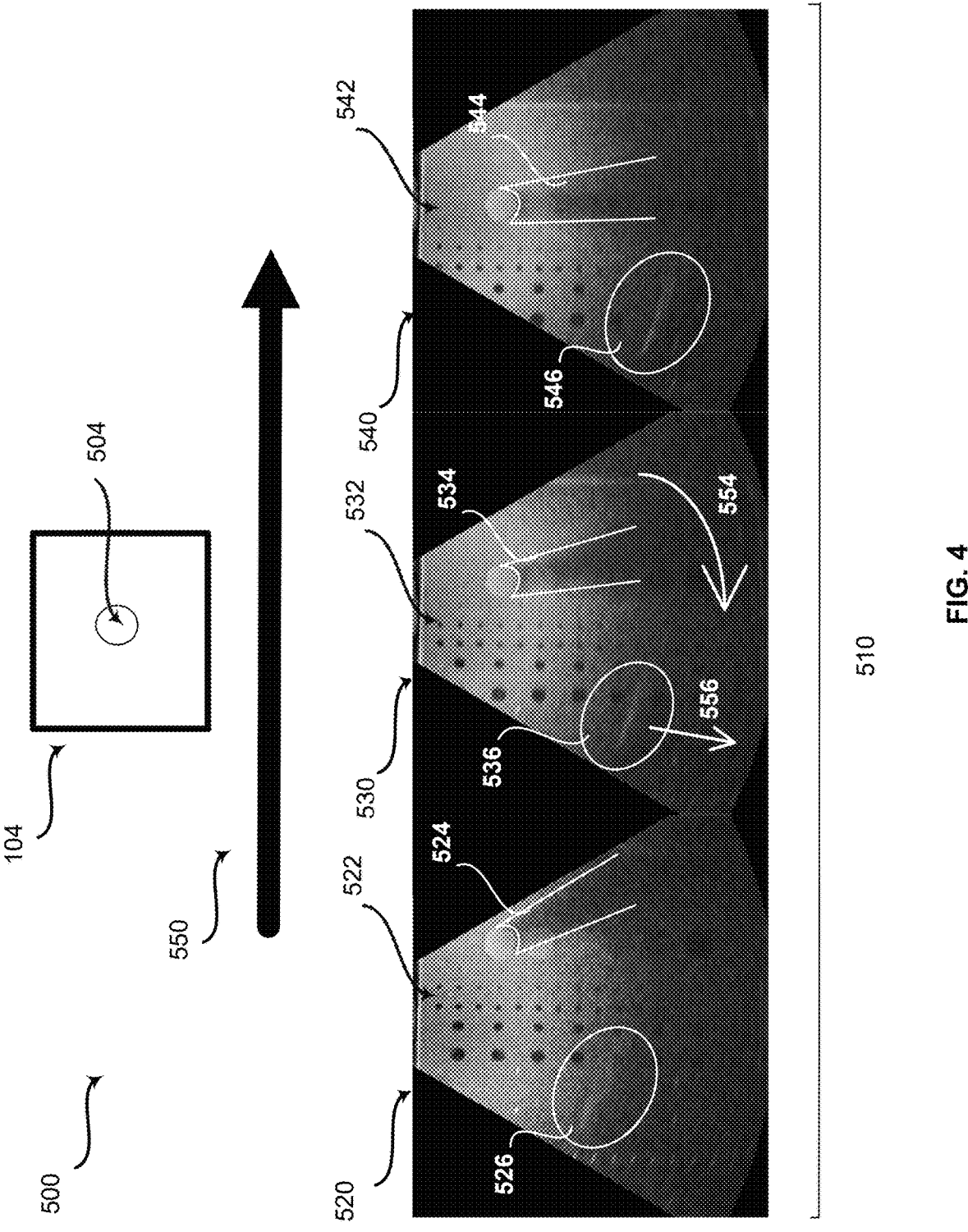
FIG. 4 is an example illustration of a sequence of ultrasound images including artifacts, in accordance with various embodiments.

FIG. 4 is an example illustration 500 of a sequence 510 of ultrasound images 520 530 540 including artifacts, in accordance with various embodiments. Ultrasound image 520 includes a phantom mimicking anatomical structure 522, a shadow 524, and a reverb 526. Ultrasound image 530 in the ultrasound sequence 510 includes a phantom representing anatomical structure 532, shadow 534, and reverb 536. Ultrasound image 540 includes a phantom representing anatomical structure 542, shadow 544, and reverb 546. As the ultrasound probe 104 moves across an anatomical structure (depicted as movement 550), the sequence 510 of ultrasound images 520 530 540 is captured. As the ultrasound images 520 530 540 are captured, artifacts such as shadows 524 534 544 and reverbs 526 536 546 may be captured by the image acquisition processor 140 in the sequence of ultrasound images. As the ultrasound probe 104 produces movement 550, shadow 524 moves as depicted by shadow 534 and then as depicted by shadow 544. Additionally and/or alternatively, as ultrasound probe 104 is moved across an anatomical structure (movement 550), reverb 526 moves as depicted by reverb 536 and then as depicted by reverb 546.

Ultrasound images 520 530 540 include non-artifact areas having a movement consistent with the movement 550 of the ultrasound probe 104. Artifacts such as shadows 524 534 544 and/or reverbs 526 536 546 do not follow the movement 550 of the ultrasound probe 104 and/or have a different movement from the movement 550 of the ultrasound probe. In some examples, shadow 524 534 544 moves in a rotational trajectory 554 around a center point 504 of the ultrasound probe 104 with movement 550 and/or around an object that casts the shadow 524 534 544. In some examples, the reverb 526 536 546 follows a different movement 556 than the ultrasound probe 104 and/or is darker than an average of an area surrounding the artifact.

In some examples, the movement detection processor 150 may be configured to detect artifacts, which are areas that are not following the main movement and/or the trajectory of the ultrasound probe 104 with the plane of acquisition, in the sequence of ultrasound images and track the movement of the artifacts. In some examples, if an artifact follows a rotational trajectory about a center of the ultrasound probe 104 and/or is darker than an average of an area surrounding the artifact, the area is identified as a shadow 414. In some examples, if the area follows a movement pattern that is different from the ultrasound probe movement and is brighter than an average of the area surrounding the artifact, the area is identified as a reverb 424. The movement of the ultrasound probe 104 and/or the movement of the artifacts calculated by the movement detection processor 150 may be stored and/or provided to the image correction processor 160. The movement of the ultrasound probe 104 and/or the movement of the artifacts calculated by the movement detection processor 150 may be stored and/or provided to the image correction processor 160.

Returning to FIG. 1, the movement detection processor 150 may comprise suitable logic, circuitry, interfaces, and/or code that may be operable to calculate movement information for artifacts in a sequence of ultrasound images obtained by the ultrasound probe 104. For example, the movement detection processor 150 may be configured to detect artifacts, which are areas that are not following the main movement and/or trajectory of the ultrasound probe 104 with the acquisition plane.

In some embodiments, detecting artifacts can be performed by, for example, computing a pixel motion seen in the sequence of ultrasound images using a motion estimation algorithm. For example, approaches such as block matching (e.g. comparing blocks of pixels to estimate motion in a sequence of ultrasound images), the Horn-Schunck method, and/or other similar methods may be used. In some examples, the ultrasound probe movement may be subtracted from an estimated motion to obtain a velocity difference at each position in the ultrasound image. In some examples, non-artifact areas of ultrasound images have a low magnitude difference. In some examples, artifacts such as shadows or reverbs tend to have larger velocity differences, particularly if including orthogonal movement areas relative to the movement of the ultrasound probe 104. In some examples, if an area follows a rotational trajectory about a center of the ultrasound probe 104 and/or is darker than an average of the surrounding area, the area is considered a shadow. In some examples, if the area follows a movement pattern that is different from the ultrasound probe movement and is brighter than an average of the surrounding area, the area is considered a reverb. The movement of the ultrasound probe 104 and/or the movement of the artifacts calculated by the movement detection processor 150 may be stored and/or provided to the image correction processor 160.

Figure 5:
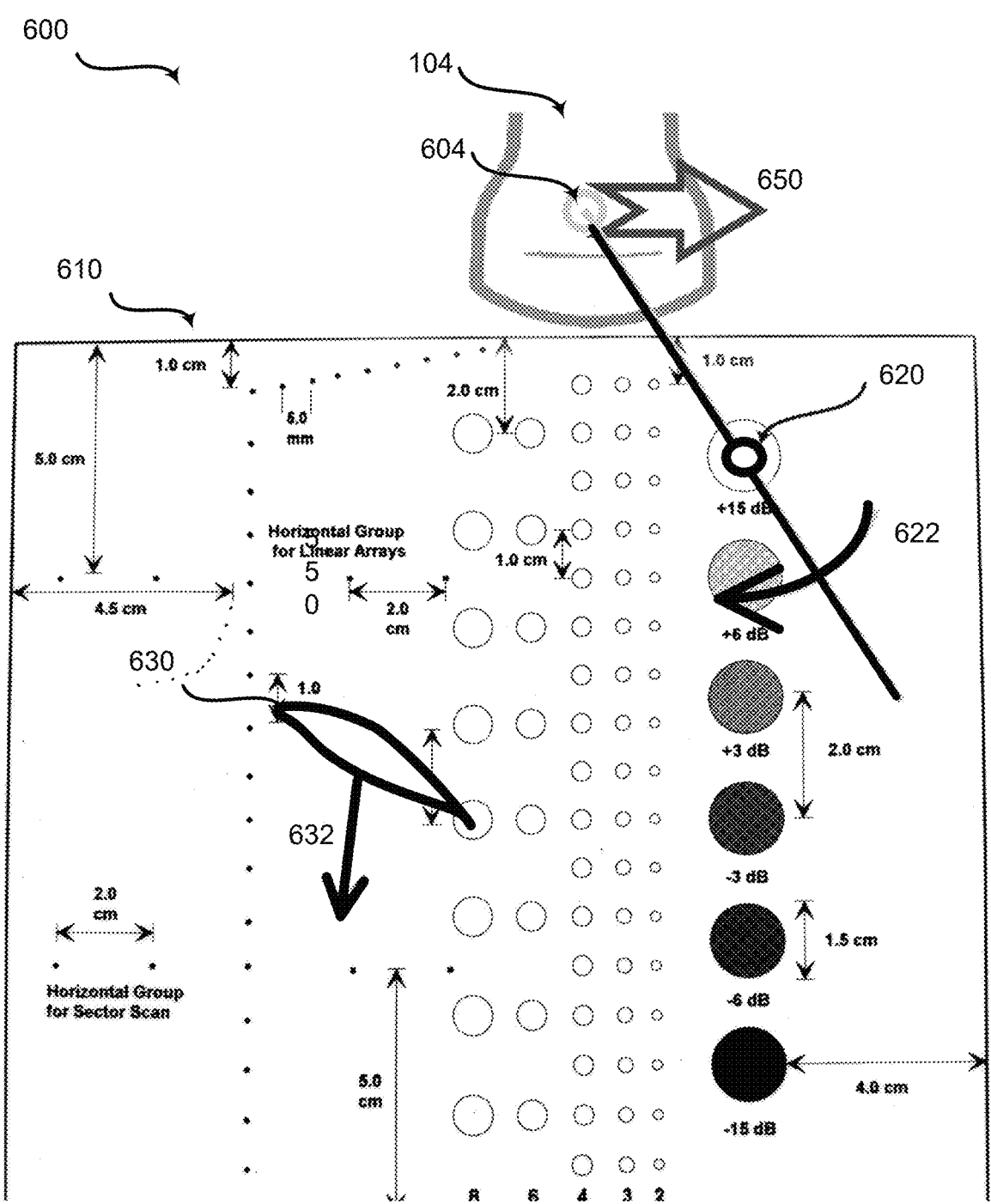
FIG. 5 is an example illustration of a schematic depicting movement of artifacts, in accordance with various embodiments.

FIG. 5 is an example illustration 600 of a schematic 610 depicting movement of artifacts, in accordance with various embodiments. FIG. 5 includes an ultrasound probe 104 with a center 604. The schematic 610 includes artifacts such as a shadow 620 and a reverb 630. As the ultrasound probe 104 moves across an acquisition plane 650, the shadow 620 may have a trajectory 622 that rotates about the center 604 of the ultrasound probe 104 and/or around an object that casts the shadow 620. The reverb 630 may have a different movement 632 from the ultrasound probe 104. Additionally and/or alternatively, the reverb movement 632 of the reverb 630 may be different from the trajectory 622 of the shadow 620.

Referring back to FIG. 1, the signal processor 132 may include an image correction processor 160 that comprises suitable logic, circuitry, interfaces, and/or code that may be operable to cause a display system 134 to present an ultrasound image based on the movement of the ultrasound probe 104 and/or the artifacts in the series of ultrasound images obtained by the image acquisition processor 140 using the ultrasound probe, in accordance with various embodiments. The movement of the sequence of ultrasound images and/or the artifacts may be received from the movement detection processor 150 and/or retrieved from the archive 138.

In some examples, the movement of the ultrasound probe and the artifacts detected by the movement processor 150 from the sequence of ultrasound images may be utilized by the image correction processor 160 to correct artifacts in the ultrasound images. For example, the image correction processor 160 may obtain the movement of the ultrasound probe 104 and the movement of the artifacts relative to an acquisition plane, and use the movement of the ultrasound probe 104 and the movement of the artifacts to correct areas including artifacts in the ultrasound images.

In some examples, the error correction processor 150 may increase the gain for artifact areas that are shadows and decrease the gain for artifact areas that are reverbs. In some examples, the error correction processor 150 may correct artifact areas using image stitching. For example, the image correction processor 160 may correct the artifact area by stitching artifact areas with portions of an ultrasound image that do not include artifact areas (non-artifact areas) in a same area where the artifact is positioned. Gain adjusting, image stitching, and/or both may be used in order to correct the sequence of ultrasound images. Additionally and/or alternatively, border smoothing may be used. The error correction processor 160 may provide the corrected ultrasound images to a user via display 134 and/or may store the corrected ultrasound images in an archive 138 and/or other computer readable medium.

Figure 6:
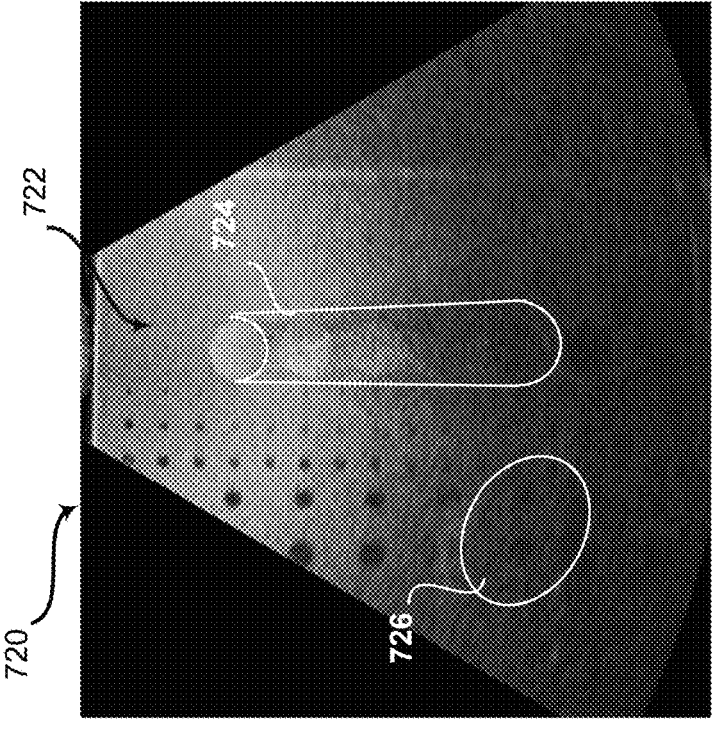
FIG. 6 provides an example illustration of corrected ultrasound images, in accordance with various embodiments.
Figure 6:
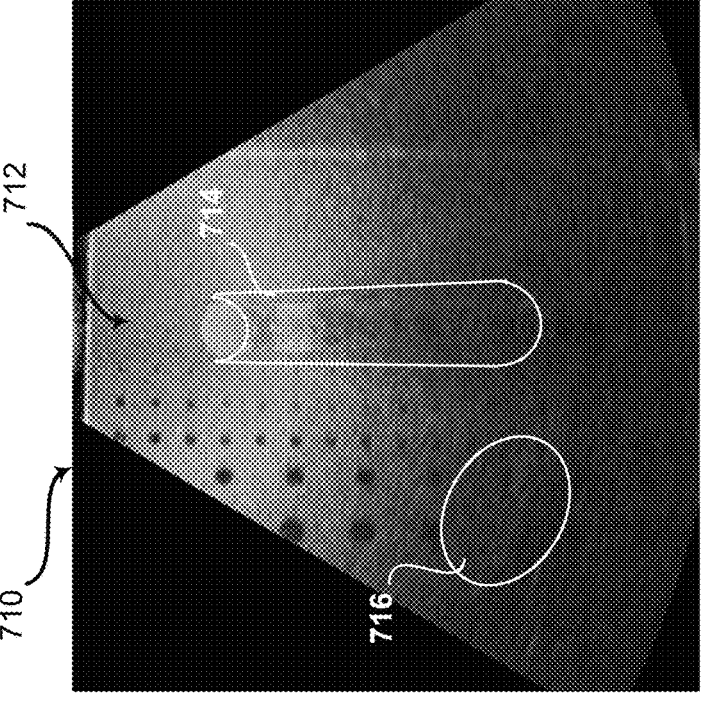

FIG. 6 provides an example illustration 700 of corrected ultrasound images 710 720, in accordance with various embodiments. Corrected ultrasound images 710 720 include phantoms representing anatomical structures 712 722, corrected areas where artifacts were identified, such as corrected shadow areas 714 724, and corrected reverb areas 716 726. In some examples, corrected shadow area 714 and corrected reverb area 716 are corrected by adjusting the gain of the corrected ultrasound image 710. For example, after artifacts are detected by the movement detection processor 150, the image correction processor 160 may correct the artifact area by adjusting the gain of the artifact area. For example, the error correction processor 150 may increase the gain for artifacts areas that are shadows and decrease the gain for artifact areas that are reverbs.

In some examples, corrected ultrasound image 720 may be an ultrasound image that is corrected using image stitching. The image correction processor 160 may correct the artifact area by stitching artifact areas with portions of an ultrasound image that do not include artifact areas in the area where the artifact is positioned. Gain adjusting, image stitching, and/or both may be used in order to correct ultrasound image to produce the corrected ultrasound images 710 720. The corrected ultrasound images 710 720 may be stored in an archive 138 and/or provided to a user on a display 134.

Referring again to FIG. 1, the display system 134 may be any device capable of communicating visual information to a user. For example, a display system 134 may include a liquid crystal display, a light emitting diode display, and/or any suitable display or displays. The display system 134 can be operable to present ultrasound images 310 410 420 520 530 540 710 720, and/or any suitable information.

The archive 138 may be one or more computer-readable memories integrated with the ultrasound system 100 and/or communicatively coupled (e.g., over a network) to the ultrasound system 100, such as a Picture Archiving and Communication System (PACS), a server, a hard disk, floppy disk, CD, CD-ROM, DVD, compact storage, flash memory, random access memory, read-only memory, electrically erasable and programmable read-only memory and/or any suitable memory. The archive 138 may include databases, libraries, sets of information, or other storage accessed by and/or incorporated with the signal processor 132, for example. The archive 138 may be able to store data temporarily or permanently, for example. The archive 138 may be capable of storing medical image data, data generated by the signal processor 132, and/or instructions readable by the signal processor 132, among other things.

In various embodiments, the archive 138 stores ultrasound images 310 410 420 520 530 540, instructions for acquiring a sequence of ultrasound images 310 410 420 520 530 540, instructions for tracking the movement 550 of the ultrasound probe 104 and the movement of the one or more artifacts, such as shadows 414 524 534 544 620, and reverbs 424 526 536 546, in the sequence of ultrasound images, instructions for identifying artifacts such as shadows 414 524 534 544 620, and reverbs 424 526 536 546 in the ultrasound images 310 410 420 520 530 540, instructions for automatically detecting displacements, rotations, and/or probe motion parameters in ultrasound images 310 410 420 520 530 540, instructions for correcting ultrasound images and producing corrected ultrasound images 710 720 with corrected shadow areas 716 726 and corrected reverb areas 714 724, and instructions for causing a display system 134 to present ultrasound images 310 410 420 520 530 540 and/or the corrected ultrasound images 710 720 with the corrected shadow areas 716 726 and corrected reverb areas 714 724.

Components of the ultrasound system 100 may be implemented in software, hardware, firmware, and/or the like. The various components of the ultrasound system 100 may be communicatively linked. Components of the ultrasound system 100 may be implemented separately and/or integrated in various forms. For example, the display system 134 and the user input device 130 may be integrated as a touchscreen display.

Still referring to FIG. 1, the training system 200 may comprise a training engine 210 and a training database 220. The training engine 210 may comprise suitable logic, circuitry, interfaces and/or code that may be operable to train the neurons of the deep neural network(s) (e.g., artificial intelligence model(s)) inferenced (i.e., deployed) by the image acquisition processor 140, the movement detection processor 150, and/or the image correction processor 160. For example, the artificial intelligence model inferenced by the movement detection processor 150 may be trained to automatically identify motion parameters from ultrasound images using database(s) 220 of classified ultrasound images of anatomical structures. As another example, the artificial intelligence model inferenced by the movement detection processor 150 and/or image correction processor 160 may be trained to automatically identify motion parameters, displacements, rotations, and the like in an ultrasound image using database(s) 220 of classified ultrasound images and/or motion parameters.

In various embodiments, the databases 220 of training images may be a Picture Archiving and Communication System (PACS), or any suitable data storage medium. In certain embodiments, the training engine 210 and/or training image databases 220 may be remote system(s) communicatively coupled via a wired or wireless connection to the ultrasound system 100 as shown in FIG. 1. Additionally and/or alternatively, components or all of the training system 200 may be integrated with the ultrasound system 100 in various forms. In some examples, the training image databases 220 may be integrated with the archive 138 or vice versa.

Figure 7:
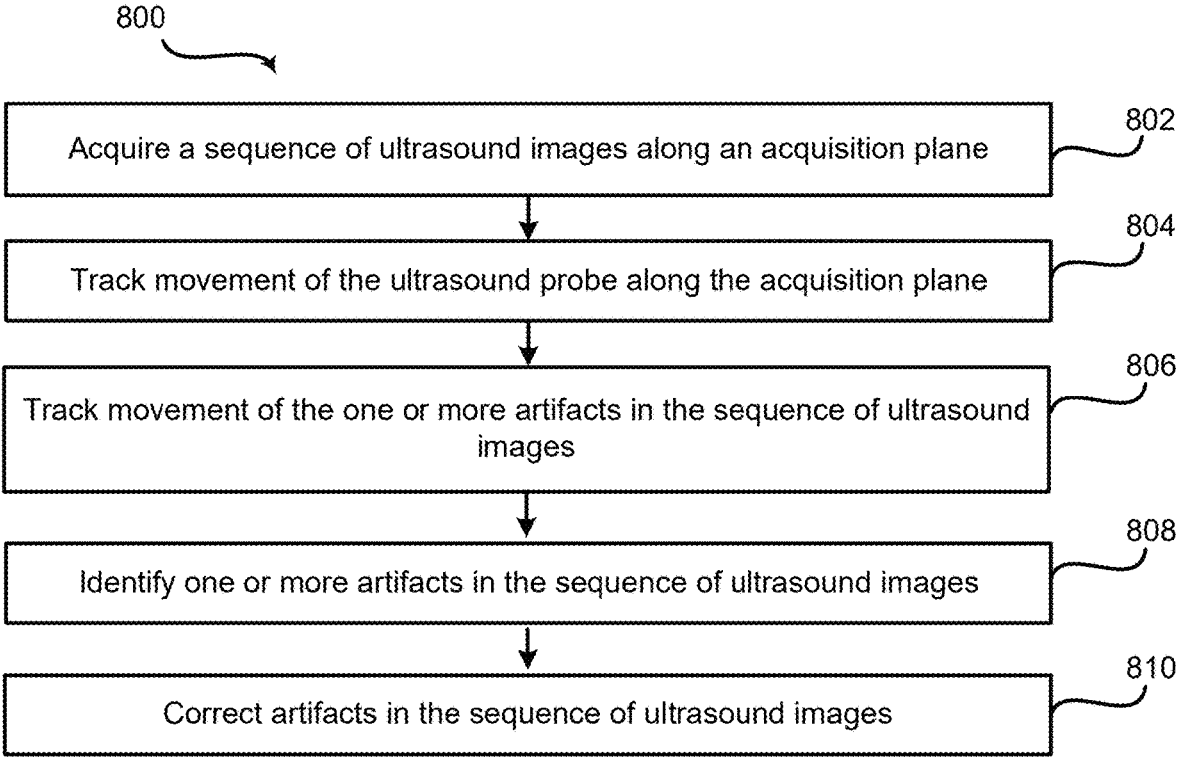
FIG. 7 is a flow chart illustrating exemplary steps 802-810 that may be utilized for obtaining ultrasound images with artifact reduction by movement detection, in accordance with various embodiments.

FIG. 7 is a flow chart 800 illustrating exemplary steps 802-810 that may be utilized for obtaining ultrasound images with artifact reduction by movement detection, in accordance with various embodiments. Certain embodiments may omit one or more of the steps, and/or perform the steps in a different order than the order listed, and/or combine certain of the steps discussed below. For example, some steps may not be performed in certain embodiments. As a further example, certain steps may be performed in a different temporal order, including simultaneously, than listed below.

At step 802, a signal processor 132, 140 of the ultrasound system 100 may be configured to acquire a sequence of ultrasound images 310 410 420 520 530 540. For example, an image acquisition processor 140 may be configured to acquire a series of ultrasound images 310 410 420 520 530 540 using an ultrasound probe 104 that is moved across an anatomical structure 312 412 422 522 532 542 712 722. The acquired ultrasound images 310 410 420 520 530 540 may be provided to the movement detection processor 150 and/or stored at archive 138 and/or any suitable computer readable medium.

At step 804, a signal processor 132, 150 of the ultrasound system 100 may be configured to track the movement 550 of the ultrasound probe 104 along the acquisition plane 650 in the ultrasound images 310 410 420 520 530 540. For example, a movement detection processor 150 may be configured to determine the movement 550 of the ultrasound probe 140 in the ultrasound images 310 410 420 520 530 540 by obtaining the movement 550 of the ultrasound probe 104 directly and/or by determining the movement 550 of the ultrasound probe 104 in the sequence of ultrasound images 310 410 420 520 530 540. The movement 550 of the ultrasound probe 104 may be stored by the movement detection processor 150 in an archive 138 or other suitable computer readable medium, and/or provided to the image correction processor 160.

At step 806, signal processor 132, 150 of the ultrasound system 100 may be configured to track the movement of artifacts in the sequence of ultrasound images 310 410 420 520 530 540. For example, the movement detection processor 150 may be configured to detect artifacts, which are areas that do not follow the main movement 550 and/or the trajectory of the ultrasound probe 104 with the plane of acquisition 650, in the sequence of ultrasound images 310 410 420 520 530 540. The movement of the artifacts such as shadows 414 524 534 544 620, and reverbs 424 526 536 546 in the ultrasound images 310 410 420 520 530 540 may be stored by the movement detection processor 150 in an archive 138 or other suitable computer readable medium, and/or provided to the image correction processor 160.

At step 808, signal processor 132, 150 of the ultrasound system 100 may be configured to identify one or more artifacts in the sequence of ultrasound images 310 410 420 520 530 540. For example, a movement detection processor 150 may be configured to determine whether artifacts are shadows 414 524 534 544 620 or reverbs 424 526 536 546 in the ultrasound images 310 410 420 520 530 540 based on the movement of the artifacts. For example, artifacts such as shadows 524 534 544 and/or reverbs 526 536 546 do not follow the movement 550 of the ultrasound probe 104 and/or have a different movement from the movement 550 of the ultrasound probe. In some examples, shadows 524 534 544 move in a rotational trajectory 554 622 around a center point 504 of the ultrasound probe 104. And reverbs 526 536 546 follow a different movement 556 632 than the ultrasound probe 104 and/or are brighter than an average of an area surrounding the artifact. The movement 550 of the ultrasound probe 104, the movement of the artifacts, and/or the identification of the artifacts may be stored by the movement detection processor 150 and/or provided to the image correction processor 160.

At step 810, a signal processor 132, 160 of the ultrasound system 100 may be configured to correct the artifacts such as shadows 414 524 534 544 620, and reverbs 424 526 536 546 in the sequence of ultrasound images 310 410 420 520 530 540. For example, the image correction processor 160 may obtain the movement 550 of the ultrasound probe 104 and the movement of the artifacts such as shadows 414 524 534 544 620 and reverbs 424 526 536 546 relative to the acquisition plane, and use the movement of the ultrasound probe 104 and the movement of the artifacts to correct artifacts in the sequence of ultrasound images 310 410 420 520 530 540 in order to produce corrected ultrasound images 710 720 including corrected artifact areas such as corrected shadow areas 714 724 and corrected reverb areas 716 726. Gain adjusting, image stitching, border smoothing, and/or a combination may be used in order to correct the sequence of ultrasound images 310 410 420 520 530 540 to produce a sequence of corrected ultrasound images 710 720. The error correction processor 160 may provide the corrected ultrasound images 710 720 to a user via display 134 for display in real-time and/or may store the corrected.

Aspects of the present disclosure provide a method 800 and system 100 for artifact reduction in ultrasound imaging comprising acquiring, by at least one processor 132 140, a sequence of ultrasound images 310 410 420 520 530 540 using an ultrasound probe 104 along an acquisition plane. The method 800 comprises tracking, by the at least one processor 132 150, a movement 550 of the ultrasound probe 104 along the acquisition plane and a movement of one or more artifacts in the sequence of ultrasound images 310 410 420 520 530 540. The method may comprise identifying, by the at least one processor 132 150, one or more artifacts in the sequence of ultrasound images 310 410 420 520 530 540 using the movement 550 of the ultrasound probe 104 along the acquisition plane and the movement of the one or more artifacts, wherein the movement of the one or more artifacts is different from the movement 550 of the ultrasound probe 104 along the acquisition plane 650, and correcting, by the at least one processor 132 160, the sequence of ultrasound images 310 410 420 520 530 540, by at least one of adjusting a gain of the artifacts or stitching artifact areas of the sequence of ultrasound images 310 410 420 520 530 540 with non-artifact areas of the sequence of ultrasound images 310 410 420 520 530 540.

In an exemplary embodiment, the method 800 comprises tracking, by the at least one processor 132 150, the movement 550 of the ultrasound probe 104 by receiving location information from the ultrasound probe 104 or by using an algorithm for detecting panning and rotation in the sequence of ultrasound images 310 410 420 520 530 540. In an exemplary embodiment, the identifying, by the at least one processor 132 150, the one or more artifacts comprises calculating pixel motion in the sequence of ultrasound images 310 410 420 520 530 540 and subtracting the movement of the ultrasound probe from the pixel motion.

In an exemplary embodiment, the one or more artifacts are shadows 414 524 534 544 620 or reverbs 424 526 536 546, and the identifying, by the at least one processor 132 150, comprises identifying the shadows 414 524 534 544 620 by determining that the one or more artifacts follow a rotational trajectory relative to a center of the ultrasound probe 104 and that the one or more artifacts are darker than an average of surrounding areas. In an exemplary embodiment, the identifying, by the at least one processor 132 150, comprises identifying the reverbs 424 526 536 546 by determining that the one or more artifacts follow a different movement pattern relative to the ultrasound probe 104 and that the one or more artifacts are brighter than the average of the surrounding areas.

In an exemplary embodiment, the one or more artifacts are shadows 414 524 534 544 620 or reverbs 424 526 536 546, and the method 800 comprises correcting, by the at least one processor 132 160, the shadows 414 524 534 544 620 by increasing the gain of the shadows 414 524 534 544 620 and correcting, by the at least one processor 132 160, the reverbs 424 526 536 546 by decreasing the gain of the reverbs 424 526 536 546. In an exemplary embodiment, the correcting, by the at least one processor 132 160, the sequence of ultrasound images 310 410 420 520 530 540, further comprises smoothing the stitched artifact areas.

Various embodiments provide an ultrasound system 100 for artifact reduction in ultrasound imaging comprising an ultrasound probe 104 configured to acquire a sequence of ultrasound images 310 410 420 520 530 540, at least one processor 132 140 configured to acquire a sequence of ultrasound images 310 410 420 520 530 540 using an ultrasound probe 104 along an acquisition plane. The at least one processor 132 150 may be configured to track a movement 550 of the ultrasound probe 104 along the acquisition plane 650 and a movement of one or more artifacts in the sequence of ultrasound images 310 410 420 520 530 540, identify the one or more artifacts in the sequence of ultrasound images 310 410 420 520 530 540 using the movement 550 of the ultrasound probe 104 along the acquisition plane with the movement of the one or more artifacts, wherein the movement of the one or more artifacts is different from the movement 550 of the ultrasound probe 104 along the acquisition plane 650. The at least one processor 132 160 may be configured to correct the sequence of ultrasound images 310 410 420 520 530 540, by at least one of adjusting a gain of the artifacts.

In a representative embodiment, the at least one processor 132 150 is configured to track the movement of the ultrasound probe by receiving location information from the ultrasound probe 104 or by using an algorithm for detecting panning and rotation in the sequence of ultrasound images 310 410 420 520 530 540. In a representative embodiment, the at least one processor 132 150 is configured to identify the one or more artifacts by calculating pixel motion in the sequence of ultrasound images 310 410 420 520 530 540 and subtracting the movement of the ultrasound probe from the pixel motion.

In a representative embodiment, the one or more artifacts are shadows 414 524 534 544 620 or reverbs 424 526 536 546, and the at least one processor 132 150 is configured to identify the shadows 414 524 534 544 620 by determining that the one or more artifacts follow a rotational trajectory relative to a center of the ultrasound probe 104 and by determining that the one or more artifacts are darker than an average of surrounding areas. In a representative embodiment, the at least one processor 132 150 is configured to identify the reverbs 424 526 536 546 by determining that the one or more artifacts follows a different movement pattern relative to the movement 550 of the ultrasound probe 104 and by determining that the one or more artifacts are brighter than the average of the surrounding areas.

In a representative embodiment, the one or more artifacts are shadows 414 524 534 544 620 or reverbs 424 526 536 546, and the at least one processor 132 160 is configured to correct the shadows 414 524 534 544 620 by increasing the gain of the shadows 414 524 534 544 620 and correct the reverbs 424 526 536 546 by decreasing the gain of the reverbs 424 526 536 546. In a representative embodiment, the at least one processor 132 160 is further configured to correct the sequence of ultrasound images 310 410 420 520 530 540 by stitching artifact areas of the sequence of ultrasound images 310 410 420 520 530 540 with non-artifact areas of the sequence of ultrasound images 310 410 420 520 530 540.

Various embodiments provide an ultrasound system 100 for artifact reduction in ultrasound imaging comprising an ultrasound probe 104 configured to acquire a sequence of ultrasound images 310 410 420 520 530 540, at least one processor 132 140 configured to acquire a sequence of ultrasound images 310 410 420 520 530 540 using an ultrasound probe 104 along an acquisition plane. The at least one processor 132 150 may be configured to track a movement 550 of the ultrasound probe 104 along the acquisition plane and a movement of one or more artifacts in the sequence of ultrasound images 310 410 420 520 530 540, identify the one or more artifacts in the sequence of ultrasound images 310 410 420 520 530 540 using the movement 550 of the ultrasound probe 104 along the acquisition plane with the movement of the one or more artifacts, wherein the movement of the one or more artifacts is different from the movement of the ultrasound probe along the acquisition plane. The at least one processor 132 160 may be configured to correct the sequence of ultrasound images 310 410 420 520 530 540 by stitching artifact areas of the sequence of ultrasound images with non-artifact areas of the sequence of ultrasound images 310 410 420 520 530 540.

In a representative embodiment, the at least one processor 132 150 is configured to track the movement of the ultrasound probe by receiving location information from the ultrasound probe 104 or by using an algorithm for detecting panning and rotation in the sequence of ultrasound images 310 410 420 520 530 540. In a representative embodiment, the at least one processor 132 150 is configured to identify the one or more artifacts by calculating pixel motion in the sequence of ultrasound images 310 410 420 520 530 540 and subtracting the movement of the ultrasound probe from the pixel motion.

In a representative embodiment, the one or more artifacts are shadows 414 524 534 544 620 or reverbs 424 526 536 546, and the at least one processor 132 150 is configured to identify the shadows 414 524 534 544 620 by determining that the one or more artifacts follow a rotational trajectory relative to a center of the ultrasound probe 104 and by determining that the one or more artifacts are darker than an average of surrounding areas. In a representative embodiment, the at least one processor 132 150 is configured to identify the reverbs 424 526 536 546 by determining that the one or more artifacts follows a different movement pattern relative to the movement 550 of the ultrasound probe 104 and by determining that the one or more artifacts are brighter than the average of the surrounding areas. In a representative embodiment, the at least one processor 132 160 is further configured to correct the sequence of ultrasound images 310 410 420 520 530 540 by adjusting a gain of the artifacts.

As utilized herein the term "circuitry" refers to physical electronic components (i.e. hardware) and any software and/or firmware ("code") which may configure the hardware, be executed by the hardware, and or otherwise be associated with the hardware. As used herein, for example, a particular processor and memory may comprise a first "circuit" when executing a first one or more lines of code and may comprise a second "circuit" when executing a second one or more lines of code. As utilized herein, "and/or" means any one or more of the items in the list joined by "and/or". As a non-limiting example, "x and/or y" means any element of the three-element set {(x), (y), (x, y), (x, z), (z, x)}. As another example, "x, y, and/or z" means any element of the seven-element set {(x), (y), (z), (x, y), (x, z), (y, z), (z, y), (x, y, z)}. As utilized herein, the term "exemplary" means serving as a non-limiting example, instance, or illustration. As utilized herein, the terms "e.g.," and "for example" set off lists of one or more non-limiting examples, instances, or illustrations. As utilized herein, circuitry is "operable" and/or "configured" to perform a function whenever the circuitry comprises the necessary hardware and code (if any is necessary) to perform the function, regardless of whether performance of the function is disabled, or not enabled, by some user-configurable setting.

Other embodiments may provide a computer readable device and/or a non-transitory computer readable medium, and/or a machine readable device and/or a non-transitory machine readable medium, having stored thereon, a machine code and/or a computer program having at least one code section executable by a machine and/or a computer, thereby causing the machine and/or computer to perform the steps as described herein for acquiring a target ultrasound image having a target view of one or more anatomical structures.

Accordingly, the present disclosure may be realized in hardware, software, or a combination of hardware and software. The present disclosure may be realized in a centralized fashion in at least one computer system, or in a distributed fashion where different elements are spread across several interconnected computer systems. Any kind of computer system or other apparatus adapted for carrying out the methods described herein is suited.

Various embodiments may also be embedded in a computer program product, which comprises all the features enabling the implementation of the methods described herein, and which when loaded in a computer system is able to carry out these methods. Computer program in the present context means any expression, in any language, code or notation, of a set of instructions intended to cause a system having an information processing capability to perform a particular function either directly or after either or both of the following: a) conversion to another language, code or notation; b) reproduction in a different material form.

While the present disclosure has been described with reference to certain embodiments, it will be understood by those skilled in the art that various changes may be made and equivalents may be substituted without departing from the scope of the present disclosure. In addition, many modifications may be made to adapt a particular situation or material to the teachings of the present disclosure without departing from its scope. Therefore, it is intended that the present disclosure not be limited to the particular embodiment disclosed, but that the present disclosure will include all embodiments falling within the scope of the appended claims.

What is claimed is:

1. A method for artifact reduction in ultrasound imaging comprising:

acquiring, by at least one processor, a sequence of ultrasound images using an ultrasound probe moved along an acquisition plane;

tracking, by the at least one processor, a movement of the ultrasound probe along the acquisition plane and a movement of one or more artifacts in the sequence of ultrasound images;

identifying, by the at least one processor, the one or more artifacts in the sequence of ultrasound images using the movement of the ultrasound probe along the acquisition plane and the movement of the one or more artifacts, wherein the movement of the one or more artifacts is different from the movement of the ultrasound probe along the acquisition plane; and providing a correction, by the at least one processor, to artifact areas in the sequence of ultrasound images based on the one or more artifacts identified in the sequence of ultrasound images.

2. The method of claim 1, wherein the tracking, by the at least one processor, the movement of the ultrasound probe is performed by receiving location information from the ultrasound probe or by using an algorithm for detecting panning and rotation in the sequence of ultrasound images.

3. The method of claim 1, wherein the identifying, by the at least one processor, the one or more artifacts comprises calculating pixel motion in the sequence of ultrasound images and subtracting the movement of the ultrasound probe from the pixel motion.

4. The method of claim 1, wherein the one or more artifacts are shadows or reverbs, and wherein the identifying, by the at least one processor, comprises identifying the shadows by determining that the one or more artifacts follow a rotational trajectory relative to a center of the ultrasound probe and that the one or more artifacts are darker than an average of surrounding areas.

5. The method of claim 4, wherein the identifying, by the at least one processor, comprises identifying the reverbs by determining that the one or more artifacts follow a different movement pattern relative to the ultrasound probe and that the one or more artifacts are brighter than the average of the surrounding areas.

6. The method of claim 1, wherein the one or more artifacts are shadows or reverbs, and wherein the method further comprises correcting, by the at least one processor, the shadows by increasing the gain of the shadows and correcting, by the at least one processor, the reverbs by decreasing the gain of the reverbs.

7. The method of claim 1, wherein the providing a correction, by the at least one processor, to artifact areas in the sequence of ultrasound images comprises adjusting a gain of the artifact areas of the one or more artifacts.

8. An ultrasound system for artifact reduction in ultrasound imaging comprising:

an ultrasound probe configured to acquire a sequence of ultrasound images;

at least one processor configured to:

acquire a sequence of ultrasound images using an ultrasound probe moved along an acquisition plane;

track a movement of the ultrasound probe along the acquisition plane and a movement of one or more artifacts in the sequence of ultrasound images;

identify the one or more artifacts in the sequence of ultrasound images using the movement of the ultrasound probe along the acquisition plane with the movement of the one or more artifacts, wherein the movement of the one or more artifacts is different from the movement of the ultrasound probe along the acquisition plane; and correct artifact areas of the sequence of ultrasound images based on the one or more artifacts identified in the sequence of ultrasound images, by at least adjusting a gain of the artifact areas of the one or more artifacts.

9. The ultrasound system of claim 8, wherein the at least one processor is configured to track the movement of the ultrasound probe by receiving location information from the ultrasound probe or by using an algorithm for detecting panning and rotation in the sequence of ultrasound images.

10. The ultrasound system of claim 8, wherein the at least one processor is configured to identify the one or more artifacts by calculating pixel motion in the sequence of ultrasound images and subtracting the movement of the ultrasound probe from the pixel motion.

11. The ultrasound system of claim 8, wherein the one or more artifacts are shadows or reverbs, and wherein the at least one processor is configured to identify the shadows by determining that the one or more artifacts follow a rotational trajectory relative to a center of the ultrasound probe and by determining that the one or more artifacts are darker than an average of surrounding areas.

12. The ultrasound system of claim 11, wherein the at least one processor is configured to identify the reverbs by determining that the one or more artifacts follows a different movement pattern relative to the movement of the ultrasound probe and by determining that the one or more artifacts are brighter than the average of the surrounding areas.

13. The ultrasound system of claim 8, wherein the one or more artifacts are shadows or reverbs, and wherein the at least one processor is configured to correct the shadows by increasing the gain of the shadows and correct the reverbs by decreasing the gain of the reverbs.

14. An ultrasound system for shadow and reverb reduction in ultrasound imaging comprising:

an ultrasound probe configured to acquire a sequence of ultrasound images;

at least one processor configured to:

acquire a sequence of ultrasound images using an ultrasound probe moved along an acquisition plane;

track a movement of the ultrasound probe along the acquisition plane and a movement of one or more artifacts in the sequence of ultrasound images;

identify the one or more artifacts in the sequence of ultrasound images using the movement of the ultrasound probe along the acquisition plane with the movement of the one or more artifacts, wherein the movement of the one or more artifacts is different from the movement of the ultrasound probe along the acquisition plane; and provide a correction of artifact areas in the sequence of ultrasound images based on the one or more artifacts identified in the sequence of ultrasound images.

15. The ultrasound system of claim 14, wherein the at least one processor is configured to track the movement of the ultrasound probe by receiving location information from the ultrasound probe or by using an algorithm for detecting panning and rotation in the sequence of ultrasound images.

16. The ultrasound system of claim 14, wherein the at least one processor is configured to identify the one or more artifacts by calculating pixel motion in the sequence of ultrasound images and subtracting the movement of the ultrasound probe from the pixel motion.

17. The ultrasound system of claim 14, wherein the one or more artifacts are shadows or reverbs, and wherein the at least one processor is configured to identify the shadows by determining that the one or more artifacts follow a rotational trajectory relative to a center of the ultrasound probe and that the one or more artifacts are darker than an average of surrounding areas.

18. The ultrasound system of claim 14, wherein the one or more artifacts are shadows or reverbs, and wherein the at least one processor is configured to identify the reverbs by determining that the one or more artifacts follow a different movement pattern relative to the movement of the ultrasound probe and that the one or more artifacts are brighter than an average of surrounding areas.

19. The ultrasound system of claim 14, wherein the at least one processor is further configured to provide the correction of the artifact areas in the sequence of ultrasound images by adjusting a gain of the artifact areas of the one or more artifacts.

* * * * *